(12) United States Patent
Guan et al.

(10) Patent No.: US 11,754,489 B2
(45) Date of Patent: Sep. 12, 2023

(54) BASELINE PULSE VALUE CALCULATION METHOD AND HEMATOLOGY ANALYZER PARTICLE COUNT METHOD

(71) Applicant: LEADWAY (HK) LIMITED, Hong Kong (CN)

(72) Inventors: Haibing Guan, Hangzhou Zhejiang (CN); Yu Xu, Hangzhou Zhejiang (CN)

(73) Assignee: LEADWAY (HK) LIMITED, Hong Kong (CN)

( * ) Notice: Subject to any disclaimer, the term of this patent is extended or adjusted under 35 U.S.C. 154(b) by 905 days.

(21) Appl. No.: 16/091,044

(22) PCT Filed: Mar. 29, 2017

(86) PCT No.: PCT/CN2017/078544
§ 371 (c)(1),
(2) Date: Oct. 3, 2018

(87) PCT Pub. No.: WO2017/167193
PCT Pub. Date: Oct. 5, 2017

(65) Prior Publication Data
US 2019/0113437 A1  Apr. 18, 2019

(30) Foreign Application Priority Data
Mar. 31, 2016  (CN) .......................... 201610199880.9

(51) Int. Cl.
*G01R 29/02*  (2006.01)
*G01N 15/14*  (2006.01)
(Continued)

(52) U.S. Cl.
CPC ....... *G01N 15/1459* (2013.01); *G01D 5/2448* (2013.01); *G01N 15/12* (2013.01);
(Continued)

(58) Field of Classification Search
CPC .... G01N 27/327; G01N 33/543; G01N 15/12; G01N 15/1429; G01N 15/1459;
(Continued)

(56) References Cited

U.S. PATENT DOCUMENTS 6,680,476 B1   1/2004  Hidalgo et al.
2009/0018799 A1*  1/2009  Huang ............... G01N 15/1429
                                                        702/190
(Continued)

FOREIGN PATENT DOCUMENTS

CN    101373593 A   2/2009
CN    102624367 A   8/2012
CN    105866011 A   8/2016

OTHER PUBLICATIONS

Extended European Search Report issued by EPO in EP 17773223 dated Oct. 21, 2019 (9 pages).
(Continued)

*Primary Examiner* — Yoshihisa Ishizuka
(74) *Attorney, Agent, or Firm* — ACUITY LAW GROUP, PC; Michael A. Whittaker

(57) ABSTRACT

A pulse baseline value calculation method and a particle counting method of a blood cell analyzer. The said pulse baseline value calculation method, within pulse non-duration time, if an absolute value of a difference value between any two adjacent data of n continuous sampled data is less than a baseline threshold, and the n continuous sampled data are closest to a pulse starting point, an average value of the n continuous sampled data is calculated, and the average value is a pulse baseline value. The present invention has the advantages of setting the baseline threshold and performing comparison, avoiding the sampled data of the baseline where the noise is superimposed, selecting the sampled data with noise or interference within an allowable range for calculation, avoiding accumulating the noise on the final
(Continued)

baseline value, making the baseline value be closer to the real data, greatly reducing the erroneous judgment of the baseline value, and making the particle count be more accurate. The method of the present invention can be applied to the particle counting of 3-diff hematology analyzers, 5-diff hematology analyzers, flow cytometers and other biochemical instruments.

6 Claims, 5 Drawing Sheets

(51) Int. Cl.
    *G01D 5/244*     (2006.01)
    *G01N 15/12*     (2006.01)
    *G16B 99/00*     (2019.01)

(52) U.S. Cl.
    CPC ......... *G01N 15/1429* (2013.01); *G01R 29/02* (2013.01); *G01N 2015/1402* (2013.01); *G01N 2015/1486* (2013.01); *G16B 99/00* (2019.02)

(58) Field of Classification Search
    CPC ... G01N 2015/1402; G01N 2015/1486; C12Q 1/00; G01D 5/2448; G01R 29/02; G16B 99/00

See application file for complete search history.

(56) References Cited

U.S. PATENT DOCUMENTS

2010/0033231 A1    2/2010  Quesada et al.
2016/0153878 A1*  6/2016  Candon ................ G01N 33/543
                                                                    435/7.4

OTHER PUBLICATIONS

Kozyrev et al., Signal processing in the calorimeter pre-trigger of the CMD-3 detector. in Nuclear Instruments and Methods in Physics Research, Section A. Jan. 2009;598(1):345-348.
International Search Report dated Jul. 11, 2017 in PCT/CN2017/078544 (6 pages).
Written Opinion dated Jul. 11, 2017 in PCT/CN2017/078544 (10 pages).
First Office Action issued by SIPO in PRC Patent Application No. CN 201610199880.9 dated Feb. 6, 2018—inc Engl lang transl (12 pages total).
Response issued to the first Office Action issued in PRC Patent Application No. CN 201610199880.9 dated May 15, 2018—inc Engl lang transl (5 pages total).
International Report of Patentability and Written Opinion issued in PCT/CN2017/078544 dated Oct. 2, 2018—inc Engl lang transl (11 pages total).

* cited by examiner

BASELINE PULSE VALUE CALCULATION METHOD AND HEMATOLOGY ANALYZER PARTICLE COUNT METHOD

CROSS-REFERENCE TO RELATED MATTERS

The present invention is filed under 35 U.S.C. § 371 as the U.S. national phase of International Patent Application No. PCT/CN2017/078544, filed Mar. 29, 2017, which designated the United States and claims priority to Chinese Patent Application No. 201610199880.9, filed Mar. 31, 2016, each of which is hereby incorporated in its entirety including all tables, figures and claims.

FIELD OF THE INVENTION

The present invention relates to the technical field of pulse signal recognition, in particular to a pulse baseline value calculation method and a particle counting method of a hematology analyzer.

BACKGROUND OF THE INVENTION

When a hematology analyzer counts the particles such as white blood cells, red blood cells and the like, a blood sample is placed in a particle measurement system, when the measured particles pass through it, a sensor generates a corresponding analog pulse signal, the signal is converted into a digital pulse signal after being amplified and filtered, the digital pulse signal includes two data states, one is data during the pulse duration, and the other is data during the pulse non-duration time. During the measurement, a baseline value, a starting point, an end point, a peak value, a valley value and the like of the pulse signal are extracted from the pulse signal, the baseline value is subtracted from the extracted peak value to obtain absolute peak value data, then the volume of the particles is obtained according to a directly proportional relation between the peak value of the pulse and the volume of the particles, and the particles are counted. If the signal is not accurately judged, the accuracy of particle counting is affected.

The Chinese patent CN201110033511.X discloses a baseline calculation module for calculating a baseline, during pulse non-duration time, the baseline calculation module performs statistics on average values of adjacent fixed number of sampling points during the pulse non-duration time to serve as a pulse baseline value, a fixed amount of sampling point data is stored by a memory, a sequence of numbers is formed by the sampling point data in a chronological order, when a new sampling point is input, the memory discards the first datum in the stored data sequence, and all remaining data is moved forward, the newly input data is arranged at the end of the data sequence, once a new sampled datum is input, the data sum of the memory of the baseline calculation module is added with the data, and the discarded data is subtracted to obtain an updated data sum, and thus a new baseline value is obtained quickly. By adoption of the above baseline calculation method, the latest baseline value can be quickly obtained, but when ripples, bubbles, jitters, sudden changes, electromagnetic interference and other noise interference cause baseline fluctuation, the noise superposed on the baseline is accumulated on the baseline value in the calculation method, thereby deviating from the real baseline value, causing misjudgment of the baseline value, affecting the calculation of the absolute pulse peak, and ultimately affecting the accuracy of the particle counting.

SUMMARY OF THE INVENTION

The technical problem to be solved by the present invention is to provide a pulse baseline value calculation method and a particle counting method of a hematology analyzer in view of the above problem that the baseline value calculation can hardly avoid the noise interference in the prior art.

In order to solve the above problem, one technical solution of the present invention is as follows:

A pulse baseline value calculation method, characterized in that, within pulse non-duration time, if an absolute value of a difference value between any two adjacent data of n continuous sampled data is less than a baseline threshold, and the n continuous sampled data are closest to a pulse starting point, an average value of the n continuous sampled data is calculated, and the average value is a pulse baseline value.

Preferably, the pulse baseline value calculation method includes the following steps:

a) presetting a memory, wherein the memory is used for storing sampled data;

b) within pulse non-duration time, receiving, by the memory, the sampled data in a chronological order of sampling, and accumulatively adding 1 to a stored data number i in the memory every time when the memory stores a sampled datum;

c) if i>1, entering step d), otherwise, returning to step b), and continuing to wait for receiving the sampled data;

d) judging whether an absolute value of a difference value between the current sampled datum and the previous sampled datum is less than a baseline threshold, if the absolute value is less than the baseline threshold, entering step e), otherwise, performing zero clearing on the ith datum in the memory and the stored data number i, then returning to step b), and restarting to receive the sampled data; and e) judging whether the stored data number i is equal to n, if i=n, calculating the average value of the n data as the current baseline value, then discarding, by the memory, the first datum and moving the other n−1 data forward, that is, storing the nth datum in the (n−1)th memory, subtracting 1 from the stored data number i, then returning to step b), and continuing to wait for receiving the sampled data; and if the stored data number i is not equal to n, directly returning to step b), and continuing to wait for receiving the sampled data.

Preferably, the sampling frequency of the n continuous sampled data is 1.5-3.5 MHz.

Preferably, the number of the n continuous sampled data is $2^m$, and the value of m is selected from 2, 3, 4 or 5.

Preferably, the baseline threshold is a preset value, and a numerical range of the baseline threshold is 10-30.

Preferably, the pulse starting point is identified according to one of the following methods: (1) if w continuous sampled data successively and progressively increase, and the difference value between the wth datum and the first datum in the w data is greater than a starting point threshold, then the pulse starting point is the first datum of the w continuous sampled data; (2) or if the jth datum of the w continuous sampled data progressively decreases, the other data progressively increase, meanwhile the (j+1)th datum is greater than the (j−1)th datum, and the difference value between the wth datum and the first datum in the w data is greater than the starting point threshold, then the pulse starting point is the first datum of the w continuous sampled data.

Preferably, the pulse starting point identification method includes the following steps:

B1) presetting a memory, wherein the memory is used for storing sampled data;

B2) receiving, by the memory, the sampled data in a chronological order of sampling, and accumulatively adding 1 to a stored data number j in the memory, namely, replacing the j with (j+1), every time when the memory stores a sampled datum;

B3) if j>1, entering step B4), otherwise, returning to step B2) and continuing to wait for receiving the sampled data;

B4) judging whether the current sampled datum $y_j$ is greater than the previous sampled datum if $y_{j-1}$, entering step B5), or, otherwise entering step B7);

B5) judging whether the stored data number j is equal to w, if j=w, entering step B6); if j is not equal to w, returning to step B2), and continuing to wait for receiving the sampled data;

B6) judging whether the difference value between the current sampled datum $y_j$ and the first datum $y_1$ in the memory is greater than the starting point threshold, if the difference value is greater than the starting point threshold, setting the first datum $y_1$ in the memory as the pulse starting point; if the difference value is smaller than the starting point threshold, discarding, by the memory, the first datum, moving the other n−1 data forward, that is, storing the wth datum in the (w−1)th memory, subtracting 1 from the stored data number j, returning to step B2), and continuing to wait for receiving the sampled data;

B7) continuing to receive, by the memory, the sampled data, accumulatively adding 1 to the stored data number j in the memory, and accumulatively adding 1 to a progressive decrease data mark q;

B8) judging whether q is equal to 1, if q=1, entering step B9), or otherwise, entering B10);

B9) judging whether the current sampled datum $y_j$ is greater than the sampled datum $y_{j-2}$, if yes, judging whether the stored data number j is equal to (w+1), if yes, replacing j with (j−1), and returning to the step B5), if not, returning to step B5), or, otherwise, entering step B10); and B10) performing zero clearing on all data in the memory, the stored data number j and the progressive decrease data mark q, returning to step B2), and restarting to receive the sampled data.

Preferably, the sampling frequency of the w continuous sampled data is 1.5-3.5 MHz, and the numerical range of w is an integer of 5-10.

Preferably, the starting point threshold is a preset value, and the numerical range of the starting point threshold is 20-60.

One technical solution of the present invention is as follows:

A particle counting method of a hematology analyzer, wherein the particle counting method includes a pulse baseline value calculation method, and within pulse non-duration time, if an absolute value of a difference value between any two adjacent data of n continuous sampled data is less than a baseline threshold, and the n continuous sampled data are closest to a pulse starting point, an average value of the n continuous sampled data is calculated, and the average value is a pulse baseline value.

Preferably, the pulse baseline value calculation method includes the following steps:

a) presetting a memory, wherein the memory is used for storing sampled data;

b) within pulse non-duration time, receiving, by the memory, the sampled data in a chronological order of sampling, and accumulatively adding 1 to a stored data number i in the memory every time when the memory stores a sampled datum;

c) if i>1, entering step d), otherwise, returning to step b), and continuing to wait for receiving the sampled data;

d) judging whether an absolute value of a difference value between the current sampled datum and the previous sampled datum is less than a baseline threshold, if the absolute value is less than the baseline threshold, entering step e), otherwise, performing zero clearing on the ith datum in the memory and the stored data number i, then returning to step b), and restarting to receive the sampled data; and e) judging whether the stored data number i is equal to n, if i=n, calculating the average value of the n data as the current baseline value, then discarding, by the memory, the first datum and moving the other n−1 data forward, that is, storing the nth datum in the (n−1)th memory, subtracting 1 from the stored data number i, then returning to step b), and continuing to wait for receiving the sampled data; and if the stored data number i is not equal to n, directly returning to step b), and continuing to wait for receiving the sampled data.

Preferably, the sampling frequency of the n continuous sampled data is 1.5-3.5 MHz.

Preferably, the number of the n continuous sampled data is $2^m$, and the value of m is selected from 2, 3, 4 or 5.

Preferably, the baseline threshold is a preset value, and a numerical range of the baseline threshold is 10-30.

Preferably, the pulse starting point is identified according to one of the following methods: (1) if w continuous sampled data successively and progressively increase, and the difference value between the wth datum and the first datum in the w data is greater than a starting point threshold, then the pulse starting point is the first datum of the w continuous sampled data; (2) or if the jth datum of the w continuous sampled data progressively decreases, the other data progressively increase, meanwhile the (j+1)th datum is greater than the (j−1)th datum, and the difference value between the wth datum and the first datum in the w data is greater than the starting point threshold, then the pulse starting point is the first datum of the w continuous sampled data.

Preferably, the pulse starting point identification method includes the following steps:

B1) presetting a memory, wherein the memory is used for storing sampled data;

B2) receiving, by the memory, the sampled data in a chronological order of sampling, and accumulatively adding 1 to a stored data number j in the memory, namely, replacing the j with (j+1), every time when the memory stores a sampled datum;

B3) if j>1, entering step B4), otherwise, returning to step B2) and continuing to wait for receiving the sampled data;

B4) judging whether the current sampled datum $y_j$ is greater than the previous sampled datum if $y_{j-1}$, entering step B5), or, otherwise entering step B7);

B5) judging whether the stored data number j is equal to w, if j=w, entering step B6); if j is not equal to w, returning to step B2), and continuing to wait for receiving the sampled data;

B6) judging whether the difference value between the current sampled datum $y_j$ and the first datum $y_1$ in the memory is greater than the starting point threshold, if the difference value is greater than the starting point threshold, setting the first datum $y_1$ in the memory as the pulse starting point; if the difference value is smaller than the starting point threshold, discarding, by the memory, the first datum, moving the other n−1 data forward, that is, storing the wth datum in the (w−1)th memory, subtracting 1 from the stored data number j, returning to step B2), and continuing to wait for receiving the sampled data;

B7) continuing to receive, by the memory, the sampled data, accumulatively adding 1 to the stored data number j in the memory, and accumulatively adding 1 to a progressive decrease data mark q;

B8) judging whether q is equal to 1, if q=1, entering step B9), or otherwise, entering B10);

B9) judging whether the current sampled datum $y_j$ is greater than the sampled datum $y_{j-2}$, if yes, judging whether the stored data number j is equal to (w+1), if yes, replacing j with (j−1), and returning to the step B5), if not, returning to step B5), or, otherwise, entering step B10); and B10) performing zero clearing on all data in the memory, the stored data number j and the progressive decrease data mark q, returning to step B2), and restarting to receive the sampled data.

Preferably, the sampling frequency of the w continuous sampled data is 1.5-3.5 MHz, and the numerical range of w is an integer of 5-10.

Preferably, the starting point threshold is a preset value, and the numerical range of the starting point threshold is 20-60.

Compared with the prior art, the pulse baseline value calculation method of the present invention has the advantages of setting the baseline threshold and performing comparison, avoiding the sampled data of the baseline where the noise is superimposed, selecting the sampled data with noise or interference within an allowable range for calculation, avoiding accumulating the noise on the final baseline value, that is, eliminating the noise interference during the baseline calculation, making the baseline value be closer to the real data, greatly reducing the erroneous judgment of the baseline value, and making the particle count be more accurate.

DETAILED DESCRIPTION OF THE EMBODIMENTS

Figure 1:
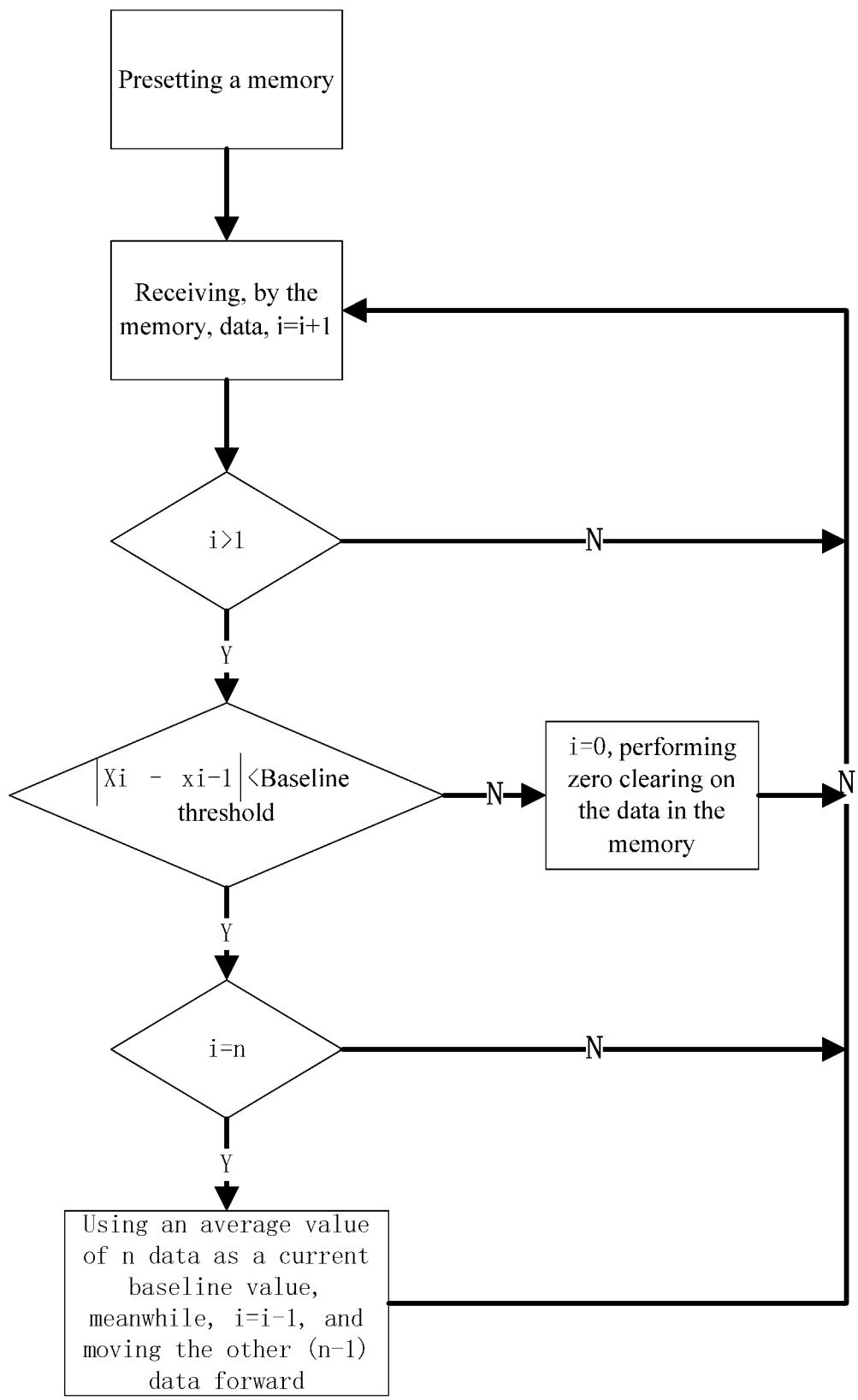
FIG. 1 is a flowchart of a pulse baseline value calculation method.

The present invention will be further described in detail below with reference to the drawings and embodiments, but the protection scope of the present invention is not limited thereto.

A particle counting method of a blood cell analyze includes a pulse identification method, and the pulse recognition method includes a pulse baseline value calculation method. During the measurement, when a blood sample passes through a micropore, it will cause impedance change to form a voltage pulse, and a pulse starting point, a pulse peak value, a baseline value and a pulse width and the like are accurately identified, and finally, particle classification statistics is performed according to an absolute amplitude of the pulse.

In a pulse baseline value calculation method, within pulse non-duration time, if an absolute value of a difference value between any two adjacent data of n continuous sampled data is less than a baseline threshold, and the n continuous sampled data are closest to a pulse starting point, an average value of the n continuous sampled data is calculated, and the average value is a pulse baseline value. The baseline threshold is a preset value and is mainly set according to the magnitude of the system noise. If the system is subjected to baseline fluctuation caused by noise such as ripple, bubbles, jitter, sudden changes, electromagnetic interference and the like, the noise is superimposed on the baseline. By adoption of the pulse baseline value calculation steps, after the baseline threshold is set and comparison is made, the sampled data of the baseline where the noise is superimposed can be avoided, the sampled data with noise or interference within an allowable range are selected for calculation, the accumulation of the noise on the final baseline value is avoided, that is, the noise interference during the baseline calculation is eliminated, the baseline value is closer to the real data, the erroneous judgment of the baseline value is greatly reduced, and the particle count is more accurate.

Preferably, the specific calculation method that the absolute value of the difference value between any two adjacent data of the n continuous sampled data is smaller than the baseline threshold is as follows: calculating the difference value between two adjacent data one by one according to the sampling time, comparing the sizes of the absolute value of the difference value and the baseline threshold one by one, and calculating all data arrays satisfying the condition that the absolute value of the difference value between any two adjacent data of the n continuous sampled data is smaller than the baseline threshold.

Preferably, the specific judgment method that the n continuous sampled data are closest to the pulse starting point is as follows: comparing time intervals of sampling time of a plurality of data arrays satisfying the condition that the absolute value of the difference value between any two adjacent data of the n continuous sampled data is smaller than the baseline threshold and the pulse starting point, and judging that the sampled data with the shortest time interval is closest to the pulse starting point. The data array further away from the pulse starting point is compared with the data arrays closest to the pulse starting point, and the average value of the data arrays closest to the pulse starting point is closer to the real baseline value of the pulse.

Referring to FIG. 1, the pulse baseline value calculation method includes the following steps:

a) presetting a memory, wherein the memory is used for storing sampled data;

b) within pulse non-duration time, receiving, by the memory, the sampled data in a chronological order of sampling, and accumulatively adding 1 to a stored data number i in the memory every time when the memory stores a sampled datum;

c) if i>1, entering step d), otherwise, returning to step b), and continuing to wait for receiving the sampled data;

d) judging whether an absolute value of a difference value between the current sampled datum and the previous sampled datum is less than a baseline threshold, if the absolute value is less than the baseline threshold, entering step e), otherwise, performing zero clearing on the ith datum in the memory and the stored data number i, then returning to step b), and restarting to receive the sampled data; and e) judging whether the stored data number i is equal to n, if i=n, calculating the average value of the n data as the current baseline value, then discarding, by the memory, the first datum and moving the other n−1 data forward, that is, storing the nth datum in the (n−1)th memory, subtracting 1 from the stored data number i, then returning to step b), and continuing to wait for receiving the sampled data; and if the stored data number i is not equal to n, directly returning to step b), and continuing to wait for receiving the sampled data.

In the pulse baseline value calculation step, the pulse starting point is also judged. Once the system detects the pulse starting point, that is, the pulse starts, the pulse baseline value calculation step stops, and the pulse baseline value is the current stored value. Within the pulse non-duration time, through the above calculation solution, there may be multiple data arrays meeting the requirements, multiple baseline values are calculated, the baseline values are covered in a chronological order, therefore, when the baseline values need to be valued, the system stores the currently latest baseline value, that is, the data array closest to the pulse starting point is selected, and the baseline value of the data array is calculated.

Preferably, the sampling frequency of the n continuous sampled data is 1.5-3.5 MHz. Preferably, the specific value of the sampling frequency is selected from one of 1.5, 1.7, 2, 2.3, 2.5, 2.8, 3, 3.2, 3.5. The sampling frequency is preset and can be set according to the system data processing requirements.

Preferably, the number of the n continuous sampled data is $2^m$, and the value of m is selected from 2, 3, 4 or 5. That is, the number of the continuous sampled data is 4, 8, 16, or 32, an even number of data are used for judgment, which is relatively simple during the calculation, is conducive to saving the CPU resources and reducing the cost of the CPU. Further, the value of n is 8.

Preferably, the baseline threshold is a preset value, and a numerical range of the baseline threshold is 10-30. Preferably, the value of the baseline threshold is selected from one of 10, 12, 14, 15, 17, 19, 20, 22, 25, 27, 29, 30. The main impact factor of the baseline threshold is system noise, the baseline threshold is preset according to the magnitude of the system noise, and during the baseline calculation, the noise interference can be excluded, so that the baseline value is closer to the true value. Further, the baseline threshold is 20.

The numerical value of the above sampling frequency, the numerical value of n, and the numerical value of the baseline threshold can be arbitrarily combined.

Embodiment 1

Figure 2:
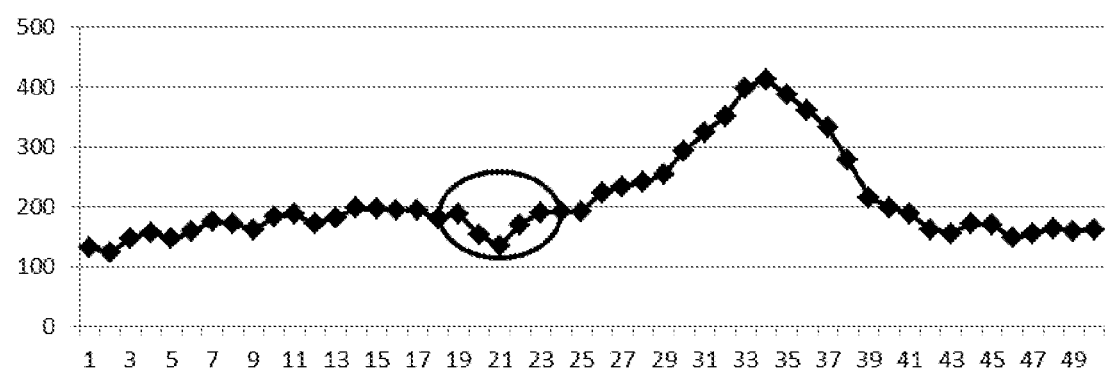
FIG. 2 is a voltage curve chart in platelet detection process in the presence of downward interference.

FIG. 2 is a voltage curve chart in a platelet detection process in the presence of downward interference, wherein the abscissa represents the number of sampled data, the vertical coordinate represents a measured voltage amplitude, the size of a pulse peak value $x_{34}$ is 413. Table 1 shows specific numerical values of sampled data $x_1$-$x_{50}$, and the data includes the sampled data within pulse non-duration time and the sampled data within pulse duration time. Taking the specific sampled data as an example to illustrate the pulse baseline value calculation steps in which the value of n is 8, the baseline threshold is 20, and the data $x_{22}$ is the pulse starting point:

1) presetting a memory, wherein the memory is used for storing 8 continuous sampled data;

2) within the pulse non-duration time, receiving, by the memory, the sampled datum $x_1$, and accumulatively adding 1 to a stored data number i in the memory, that is, i=1, i<1;

3) receiving, by the memory, the sampled datum $x_2$, i=2, $x_2$-$x_1$=124-133=−9, wherein the absolute value of the difference value is less than the baseline threshold 20, i<8;

4) receiving, by the memory, the sampled datum $x_3$, i=3, $x_3$-$x_2$=147-124=23, wherein the absolute value of the difference value is greater than the baseline threshold of 20;

5) i=0, performing zero clearing on the data of the memory;

6) restarting to receive the sampled datum $x_4$, i=1, i<1;

7) receiving, by the memory, the sampled datum $x_5$, i=2, $x_5$-$x_4$=146-158=−12, wherein the absolute value of the difference value is less than the baseline threshold 20, i<8;

8) receiving, by the memory, the sampled datum $x_6$, i=3;

... omitting the specific judgment steps of $x_s$ to $x_{10}$;

H1) $x_{10}$-$x_9$=183-162=21, the absolute value of the difference value being greater than the baseline threshold of 20, i=0, performing zero clearing on the data of the memory H2) restarting to receive the sampled datum $x_{11}$, i=1, i<1;

H3) receiving, by the memory, the sampled datum $x_{12}$, i=2, $x_{12}$-$x_{11}$=172-187=−15, wherein the absolute value is less than the baseline threshold of 20, i<8;

H4) receiving, by the memory, the sampled datum $x_{13}$, i=3, $x_{13}$-$x_{12}$=182-172=10, wherein the absolute value is less than the baseline threshold 20, i<8;

H5) receiving, by the memory, the sampled datum $x_{14}$, i=4, $x_{14}$-$x_{13}$=198-182=16, wherein the absolute value is less than the baseline threshold of 20, i<8;

H6) receiving, by the memory, the sampled datum $x_{15}$, i=5, $x_{15}$-$x_{14}$=196-198=−2, wherein the absolute value is less than the baseline threshold 20, i<8;

H7) receiving, by the memory, the sampled datum $x_{16}$, i=6, $x_{16}$-$x_{15}$=195-196=−1, wherein the absolute value is less than the baseline threshold of 20, i<8;

H8) receiving, by the memory, the sampled datum $x_{17}$, i=7, $x_{17}$-$x_{16}$=194-195=−1, wherein the absolute value is less than the baseline threshold of 20, i<8;

H9) receiving, by the memory, the sampled datum $x_{18}$, i=8, $x_{18}$-$x_{17}$=180-194=−14, wherein the absolute value is less than the baseline threshold 20;

H10) calculating the average value 188 of 8 data of $x_{11}$ to $x_{18}$ as the current baseline value and storing the same, meanwhile, discarding, by the memory, the first datum $x_{11}$, and moving the other 7 data forward, that is, storing the nth datum in the (n−1) memory, wherein the stored data number i=7;

H11) receiving, by the memory, the sampled datum $x_{19}$, i=8, $x_{19}$-$x_{18}$=188-180=8, wherein the absolute value is less than the baseline threshold 20;

H12) calculating the average value 188.12 of 8 data of $x_{12}$ to $x_{19}$ as the current baseline value and storing the same, covering the previously calculated baseline value, meanwhile, discarding, by the memory, the first datum $x_{12}$, and moving the other 7 data forward, that is, storing the nth datum in the (n−1) memory, wherein the stored data number i=7;

H13) receiving, by the memory, the sampled datum $x_{20}$, i=8, $x_{20}$-$x_{19}$=152-188=−36, wherein the absolute value is greater than the baseline threshold 20, i=0, and performing zero clearing on the data of the memory;

omitting the specific judgment steps of $x_{20}$ to the pulse starting point; and continuing the detection, if a new baseline value meeting the condition, continuously covering the new baseline value, until the pulse starting point $x_{22}$ is detected, stopping calculating the baseline value, and if it is discovered by calculation that no baseline value between $x_{20}$ and $x_{22}$ can meet the baseline value calculation condition, using the average value 188.12 of 8 data from $x_{12}$ to $x_{19}$ as the baseline value of the current pulse.

TABLE 1

50 sampled data of pulse voltage with downward interference

| Serial number | $x_1$-$x_{10}$ | $x_{11}$-$x_{20}$ | $x_{21}$-$x_{30}$ | $x_{31}$-$x_{40}$ | $x_{41}$-$x_{50}$ |
|---|---|---|---|---|---|
| 1 | 133 | 187 | 135 | 324 | 187 |
| 2 | 124 | 172 | 170 | 351 | 162 |
| 3 | 147 | 182 | 190 | 398 | 156 |
| 4 | 158 | 198 | 192 | 413 | 172 |
| 5 | 146 | 196 | 193 | 387 | 170 |
| 6 | 159 | 195 | 223 | 361 | 148 |
| 7 | 176 | 194 | 234 | 332 | 156 |
| 8 | 171 | 180 | 241 | 278 | 164 |
| 9 | 162 | 188 | 254 | 215 | 160 |
| 10 | 183 | 152 | 293 | 199 | 162 |

Referring to Table 2, in the prior art, if only a plurality of numerical values before the pulse starting point are averaged, if the value is 8, then the pulse baseline value is the average value 179.75 of 8 data from $x_{14}$ to $x_{21}$. It can be clearly seen in an area marked by a black circle in FIG. 2 that the voltage curve has a downward interference before the starting of the pulse, the interference is within the interval of $x_{20}$ to $x_{22}$, in the method of the prior art, the interference in the circle is calculated within the baseline value, however, the value interval of the baseline value calculation of the present invention is $x_{12}$ to $x_{19}$, thereby avoiding the interference interval. Due to the difference of the value range, the deviation of the baseline value affects the accuracy of the absolute peak value, and the percentage of the absolute peak value in the two cases is 3.6%, which directly affects the measurement of the volume of the cell and the related distribution parameters.

TABLE 2 comparison of baseline value calculation results

| | Baseline value | Value area | Absolute peak value | Percentage |
|---|---|---|---|---|
| Method of the present invention | 188.12 | $x_{12}$ to $x_{19}$ | 224.88 | 3.6% |
| Prior art | 179.75 | $x_{14}$ to $x_{21}$ | 233.25 | |

Figure 3:
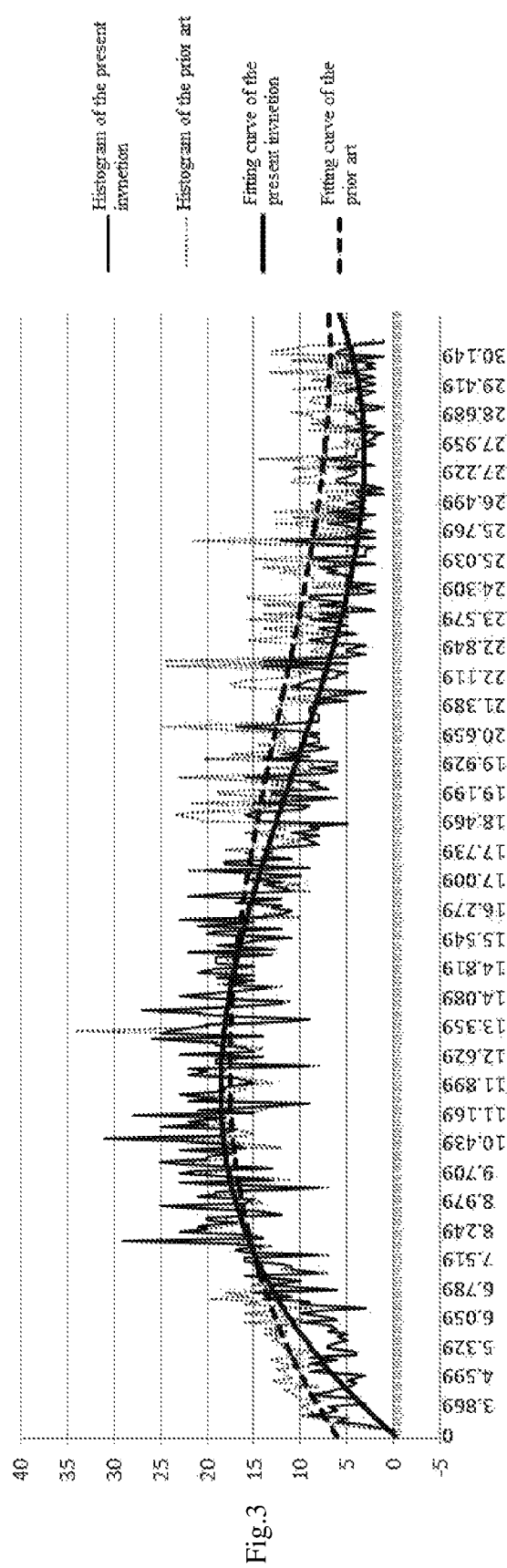
FIG. 3 is a histogram of blood platelet distribution in a 3-diff hematology analyzer.

Referring to FIG. 3, it is a histogram of blood platelet distribution widths at 2-30 fl obtained by the method of the present invention and the method of the prior art, when the same sample of the equal volume is detected under the same conditions. In FIG. 3, abscissa represents a cell volume value (in fl), and the vertical coordinate represents a cell number value; a thin solid line represents a histogram obtained by the method of the present invention, and a thick solid line represents a curve obtained by polynomial fitting of the histogram according to the present invention; and a thin dashed line represents a histogram obtained by the method of the prior art, and a thick dashed line represents a curve obtained by polynomial fitting of the histogram of the prior art.

In the detection of a 3-diff hematology analyzer, the distribution width PDW of blood platelets is generally 2-30 fl, and it can be seen from the comparison of the thick solid line and the thick broken line that, when the baseline calculation is inaccurate, the distribution width of the histogram is widened, when the cell volume calculation is relatively small, the histogram is stretched to the left side, and when the cell volume calculation is relatively large, the histogram is stretched to the right side, that is, the cell count values falling within 2-30 fl are fewer. As shown in FIG. 3, when the abscissa is 2 fl, the cell distribution of the thick solid line on the point is relatively small, and the cell distribution of the thick dashed line on the coordinate is relatively large, some of cells are distributed before the 2 fl, in other words, the distribution width of the thick dotted line histogram is widened, at this time, the cell distribution amount and volume are deviated, that is, some cells in the thick dotted line are distributed at the outside of the distribution width PDW of the blood platelets. As shown in Table 2, the baseline value in the prior art is relatively small, resulting in a relatively high absolute peak value of the cell, that is, the cell volume value is relatively large, so that some cells are distributed at the outside of the cell distribution width, resulting in inaccurate cell counting, and even causing erroneous judgment. If the baseline value is relatively large, the cell volume value is relatively small, and some cells are still distributed at the outside of the cell distribution width.

Embodiment 2

Figure 4:
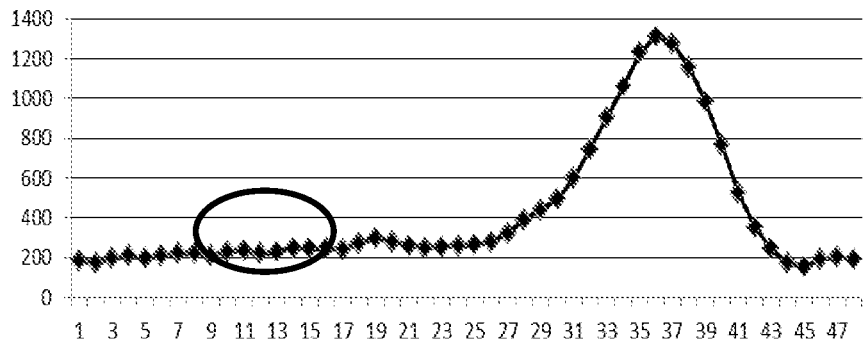
FIG. 4 is a voltage curve chart in red blood cell detection process in the presence of upward interference.

FIG. 4 is a voltage curve chart in a red blood cell detection process in the presence of upward interference, wherein the abscissa represents the number of sampled data, the vertical coordinate represents a measured voltage amplitude, the size of a pulse peak value $x_{36}$ is 1314. Calculation is performed in such a manner that value of n is 8, the baseline threshold is 20, and the data $x_{23}$ is the pulse starting point. Table 3 shows specific numerical values of sampled data $x_1$-$x_{50}$ in FIG. 4, and the data include the sampled data within pulse non-duration time and the sampled data within pulse duration time. Through the calculation, it can be obtained that the data range of the sampled data meets the requirements of baseline value calculation from $x_{10}$ to $x_{17}$, and therefore, the average value 238.12 of 8 data in $x_{10}$ to $x_{17}$ is used as the baseline value of the current pulse.

TABLE 3

50 sampled data of pulse voltage with upward interference

| Serial number | $x_1$-$x_{10}$ | $x_{11}$-$x_{20}$ | $x_{21}$-$x_{30}$ | $x_{31}$-$x_{40}$ | $x_{41}$-$x_{50}$ |
|---|---|---|---|---|---|
| 1 | 183 | 237 | 262 | 599 | 525 |
| 2 | 174 | 222 | 250 | 744 | 355 |
| 3 | 197 | 232 | 255 | 903 | 246 |
| 4 | 208 | 248 | 260 | 1063 | 171 |
| 5 | 196 | 246 | 265 | 1229 | 156 |
| 6 | 209 | 245 | 280 | 1314 | 191 |
| 7 | 226 | 244 | 325 | 1277 | 206 |
| 8 | 221 | 270 | 390 | 1156 | 191 |
| 9 | 212 | 300 | 440 | 986 | 525 |
| 10 | 231 | 280 | 494 | 766 | 355 |

Referring to Table 4, in the prior art, if only a plurality of numerical values before the pulse starting point are averaged, if the value is 8, then the pulse baseline value is the average value 262.12 of 8 data from $x_{15}$ to $x_{22}$. It can be clearly seen in an area marked by a black circle in FIG. 4 that the voltage curve has an upward interference before the starting of the pulse, the interference is within the interval of $x_{18}$ to $x_{20}$, in the method of the prior art, the interference in the circle is calculated within the baseline value, however, the value interval of the baseline value calculation of the present invention is $x_{10}$ to $x_{17}$, thereby avoiding the interference interval. Due to the difference of the value range, the deviation of the baseline value affects the accuracy of the absolute peak value, and the percentage of the absolute peak value is 2.28%, which directly affects the measurement of the volume of the cell and the related distribution parameters. That is, the baseline value of the prior art is relatively large, then the absolute peak value is relatively small, the cell volume is relatively small, and the distribution can be beyond the cell distribution width.

TABLE 4 comparison of baseline value calculation results

| | Baseline value | Value area | Absolute peak value | Percentage |
|---|---|---|---|---|
| Method of the present invention | 238.12 | $x_{10}$ to $x_{17}$ | 1075.88 | 2.28% |
| Prior art | 262.12 | $x_{15}$ to $x_{22}$ | 1051.88 | |

Tests and calculation prove that the combination of any three numerical values of the value range of the sampling frequency of 1.5-3.5 MHz, the numerical range of n of 4, 8, 16 or 32 and the numerical range of the baseline threshold of 10-30, for example, the combination in which the sampling frequency is 1.5 MHz, the value of n is 8 and the baseline threshold is 30; or the combination in which the sampling frequency is 2.3 MHz, the value of n is 16 and the baseline threshold is 15; or combination in which the sampling frequency is 3 MHz, the value of n is 32 and the baseline threshold is 22; or a combination in which the sampling frequency is 3.5 MHz, the value of n is 4 and the baseline threshold is 10; can all avoid the sampled data of the baseline where the noise is superimposed, selecting the sampled data with noise or interference within an allowable range for calculation, eliminating the noise interference during the baseline calculation, making the baseline value be closer to the real data, greatly reducing the erroneous judgment of the baseline value, and making the particle count be more accurate.

The pulse starting point is identified according to one of the following methods: (1) if w continuous sampled data successively and progressively increase, and the difference value between the wth datum and the first datum in the w data is greater than a starting point threshold, then the pulse starting point is the first datum of the w continuous sampled data; (2) or if the jth datum of the w continuous sampled data progressively decreases, the other data progressively increase, meanwhile the (j+1)th datum is greater than the (j−1)th datum, and the difference value between the wth datum and the first datum in the w data is greater than the starting point threshold, then the pulse starting point is the first datum of the w continuous sampled data. The starting point is the first datum of the w data, compared with other data in the w data, the starting point is more stable, therefore when the difference value between the with datum and the first datum is compared with the starting point threshold, the accuracy is higher. In the presence of interference during the judgment of the pulse starting point, the w continuous sampled data are difficult to successively and progressively increase, some of the data may progressively decrease, erroneous judgment is generated easily by only adopting the successive and progressive mode of the w data, thereby affecting the accuracy of the pulse width calculation, so the solution in which the jth datum of the w continuous sampled data progressively decreases is adopted, and by combination of the two solutions, the pulse starting point is accurately judged without generating erroneous judgment on the location of the pulse starting point due to the presence of the interference.

Figure 5:
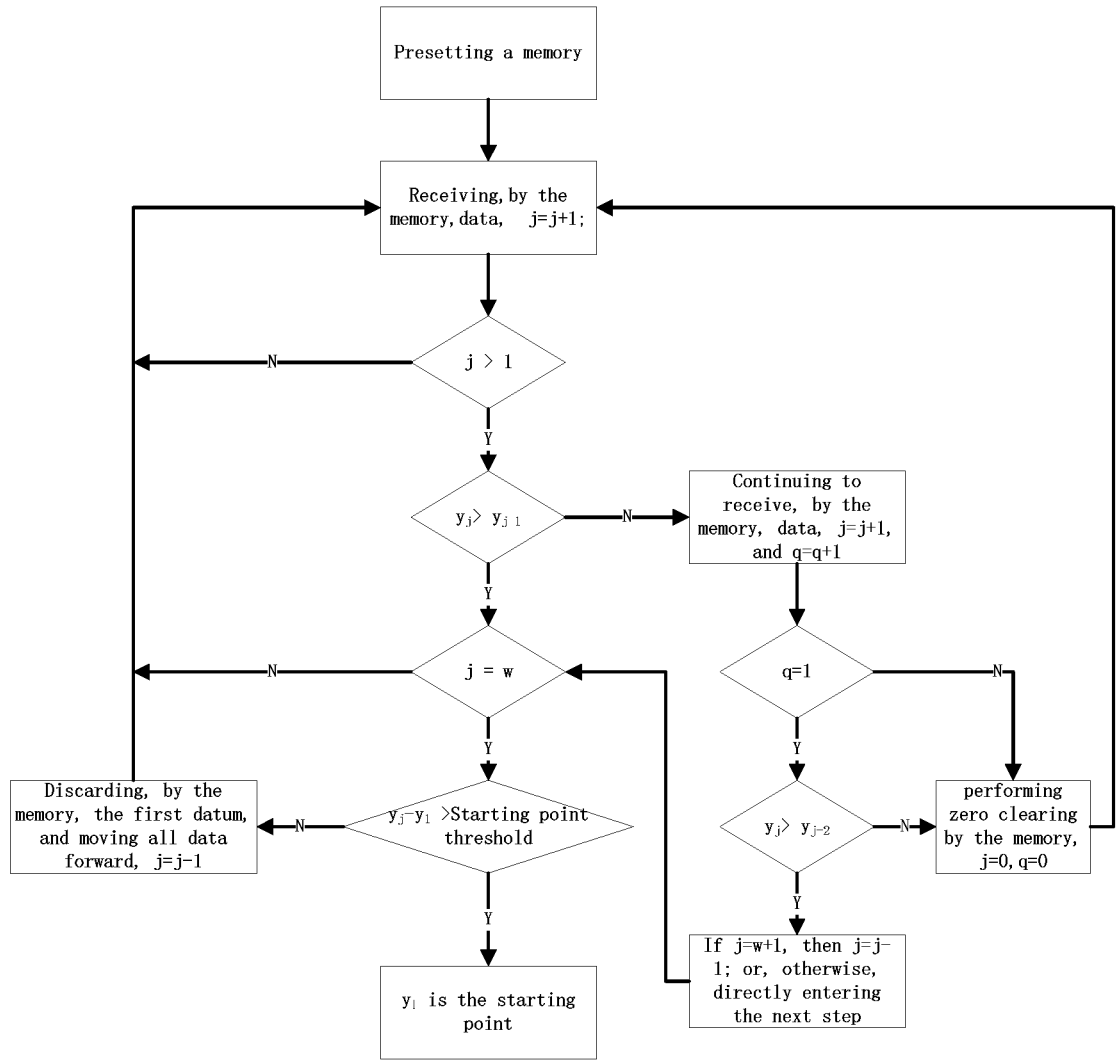
FIG. 5 is a flowchart of a pulse starting point identification step.

Referring to FIG. 5, the pulse starting point identification method includes the following steps:

B1) presetting a memory, the memory is used for storing (w+1) continuous sampled data;

B2) receiving, by the memory, the sampled data in a chronological order of sampling, and accumulatively adding 1 to a stored data number j in the memory, namely, j=j+1, every time when the memory stores a sampled datum;

B3) if j>1, entering step B4), otherwise, returning to step B2) and continuing to wait for receiving the sampled data;

B4) judging whether the current sampled datum $y_j$ is greater than the previous sampled datum if $y_{j-1}$, entering step B5), or, otherwise entering step B7);

B5) judging whether the j is equal to w, if j=w, entering step B6); if j is not equal to w, returning to step B2), and continuing to wait for receiving the sampled data;

B6) judging whether the difference value between the current sampled datum $y_j$ and the first datum $y_1$ in the memory is greater than the starting point threshold, if the difference value is greater than the starting point threshold, setting the first datum $y_1$ in the memory as the pulse starting point; if the difference value is smaller than the starting point threshold, discarding, by the memory, the first datum, moving the other w−1 data forward, that is, storing the wth datum in the (w−1)th memory, subtracting 1 from the stored data number j, returning to step B2), and continuing to wait for receiving the sampled data;

B7) continuing to receive, by the memory, the sampled data, accumulatively adding 1 to the stored data number j in the memory, and accumulatively adding 1 to a progressive decrease data mark q;

B8) judging whether q is equal to 1, if q=1, entering step B9), or otherwise, entering B10);

B9) judging whether the current sampled datum $y_j$ is greater than the sampled datum $y_{j-2}$, if yes, judging whether j is equal to w+1, if yes, j=j−1, and returning to the step B5), if not, returning to step B5), or, otherwise, entering step B10); and B10) performing zero clearing on all data in the memory, the stored data number j and the progressive decrease data mark q, returning to step B2), and restarting to receive the sampled data.

Preferably, the sampling frequency of the w continuous sampled data is 1.5-3.5 MHz, and the numerical range of w is an integer of 5-10. Preferably, the specific value of the sampling frequency is selected from one of 1.5, 1.7, 2, 2.3, 2.5, 2.8, 3, 3.2, 3.5, and the numerical value of w is selected from one of 5, 6, 7, 8, 9, and 10. Further, the numerical value of w is 7.

Preferably, the starting point threshold is a preset value, and the numerical range of the starting point threshold is 20-60. Preferably, the numerical value of the starting point threshold is selected from one of 20, 22, 24, 25, 27, 29, 30, 32, 35, 37, 39, 40, 43, 45, 48, 50, 52, 55, 57, 60. Further, the starting point threshold is 40. The main influence factor of the starting point threshold is the system noise, the starting point threshold is preset according to the magnitude of the system noise, and when the starting point threshold is detected, the interference of the noise interference can be removed, and the pulse starting point can be accurately detected.

The numerical value of the sampling frequency, the numerical value of w and the numerical value of the starting point threshold can be randomly combined.

Embodiment 3

Figure 6:
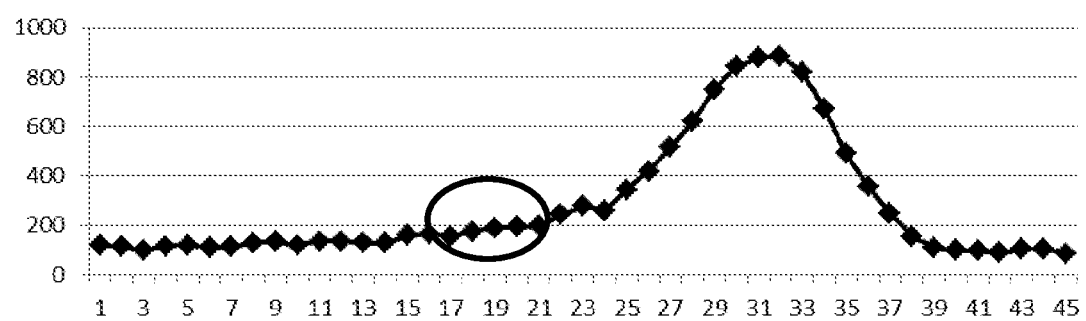
FIG. 6 is a voltage curve chart in a pulse starting point identification process in the presence of upward interference.

FIG. 6 is a voltage curve chart in a red blood cell detection process in the presence of downward interference, wherein the abscissa represents the number of sampled data, the vertical coordinate represents a voltage amplitude, the size of a pulse peak value $x_{32}$ is 884, Table 5 shows specific numerical values of sampled data $x_1$-$x_{45}$, and the data include the sampled data within pulse non-duration time and the sampled data within pulse duration time. The calculation steps of the pulse starting point by taking specific sampled data as an example in which the numerical value of w is 7 and the starting point threshold is 40:

1) presetting a memory, wherein the memory is used for storing 8 continuous sampled data;
2) receiving and storing, by the memory, the sampled datum $y_1=x_1=121$, and accumulatively adding 1 to a stored data number j in the memory, that is, j=1;
3) receiving, by the memory, the sampled datum $y_2=x_2=112$, j=2, $y_2<y_1$, and receiving, by the memory, the sampled datum $y_3=x_3=97$, j=3, q=1;
4) $y_3<y_1$, performing zero clearing on the data of the memory, j=0, q=0; ... omitting the specific judgment steps of $x_4$ to $x_{12}$;
  G1) receiving, by the memory, the sampled datum $y_1=x_{13}=129$, j=1;
  G2) receiving, by the memory, the sampled datum $y_2=x_{14}=127$, j=2, $y_2<y_1$, and receiving, by the memory, the sampled datum $y_3=x_{15}=157$, j=3, q=1;
  G3) $y_3>y_1$, receiving, by the memory, the sampled datum $y_4=x_{16}=165$, j=4;
  G4) $y_4>y_3$, receiving, by the memory, the sampled datum $y_5=x_{17}=154$, j=5;
  G5) $y_4>y_3$, performing zero clearing on the data of the memory, j=0, q=0;
  G6) receiving and storing, by the memory, sampled datum $y_1=x_{18}$ 174, and accumulatively adding 1 to a stored data number j in the memory, that is, j=1;
  G7) receiving, by the memory, the sampled datum $y_2=x_{19}=191$, j=2, $y_2>y_1$;
  G8) receiving, by the memory, the sampled datum $y_3=x_{20}=193$, j=3; $y_3>y_2$;
  G9) receiving, by the memory, the sampled datum $y_4=x_{21}=197$, j=4, $y_4>y_3$;
  G10) receiving, by the memory, the sampled datum $y_5=x_{22}=243$, j=5, $y_5>y_4$;
  G11) receiving, by the memory, the sampling data $y_6=x_{23}=278$, j=6, $y_6>y_5$;
  G12) receiving, by the memory, the sampling data $y_7=x_{24}=260$, j=7, $y_7<y_6$;
  G13) receiving, by the memory, the sampling data $y_8=x_{25}=344$, j=8, q=1; $y_8>y_6$; and
  G14) j=j−1=7, $y_7-y_1=x_{24}-x_{18}=260-174=86$, greater than the starting point threshold 40, $y_1$, namely, $x_{18}$ being the pulse starting point.

Through calculation, the obtained data range of the sampled data meets the calculation requirements of the pulse starting point from $x_{18}$ to $x_{24}$, therefore, the $x_{18}$ is the starting point of the current pulse. Referring to FIG. 6, in the calculation process of the pulse starting point, if the pulse interference is encountered, the situation that individual sampling points are progressively decreased from the beginning of the pulse starting point, it can be clearly seen from a site marked by a black circle in FIG. 6 that an obvious drop occurs at the $x_{24}$ point, all data in front of the $x_{24}$ point are removed very easily if the method in the prior art is applied to the calculation, the $x_{24}$ point is deemed as the pulse starting point, but the actual pulse starting point is $x_{18}$, thus affecting the accuracy of the pulse width calculation.

TABLE 5

45 sampled data in the pulse identification process

| Serial number | $x_1$-$x_{10}$ | $x_{11}$-$x_{20}$ | $x_{21}$-$x_{30}$ | $x_{31}$-$x_{40}$ | $x_{41}$-$x_{45}$ |
|---|---|---|---|---|---|
| 1 | 121 | 136 | 197 | 877 | 97 |
| 2 | 112 | 135 | 243 | 884 | 89 |
| 3 | 97 | 129 | 278 | 819 | 104 |
| 4 | 115 | 127 | 260 | 669 | 106 |
| 5 | 120 | 157 | 344 | 490 | 86 |
| 6 | 109 | 165 | 419 | 359 | |
| 7 | 112 | 154 | 514 | 248 | |
| 8 | 130 | 174 | 621 | 156 | |
| 9 | 133 | 191 | 751 | 109 | |
| 10 | 120 | 193 | 842 | 99 | |

Tests and calculation prove that the combination of any three numerical values of value range of the sampling frequency of 1.5-3.5 MHz, the numerical range of w of 5-10 and the numerical range of the starting point threshold of 20-60, for example, the combination in which the sampling frequency is 1.5, the value of w is 10 and the starting point threshold is 27; or the combination in which the sampling frequency is 2, the value of w is 7 and the starting point threshold is 60; or combination in which the sampling frequency is 2.8, the value of w is 9 and the starting point threshold is 20; or a combination in which the sampling frequency is 3.5, the value of w is 5 and the starting point threshold is 43; can all avoid the specific sampled data with pulse interference and accurately calculate the pulse starting point.

What is claimed is:

1. A pulse baseline voltage value calculation method operating on a hematology analyzer, comprising
  initiating a particle counting analysis method operating on the hematology analyzer, and during operation of the particle counting analysis method,
    (i) assigning a pre-determined voltage value v as a pulse baseline difference threshold value and a pre-determined sample number value n as a number of consecutive sampled voltage values to be used to determine the pulse baseline voltage value, wherein n is an integer greater than 1; and
    (ii) sampling and processing consecutive voltage values indicative of a blood sample passing through a micropore in the hematology analyzer, wherein particles in the blood sample cause a change in voltage values generated from the hematology analyzer, at a sampling frequency of from 1.5 to 3.5 MHz by
      (a) setting a counter i=1,
      (b) obtaining voltage value i by sampling a first voltage value according to the sampling frequency from the hematology analyzer, and storing the sampled voltage value i in memory location L(i),
      (c) obtaining voltage value i+1 by sampling a second voltage value according to the sampling frequency from the hematology analyzer and storing the sampled voltage value i+1 in memory location L(i+1), and (d) processing the stored voltage values by calculating an absolute value of the difference between the voltage value stored in memory location L(i) and the voltage value stored in memory location L(i+1), wherein if the absolute value of the difference between the voltage value stored in memory location L(i) and the voltage value stored in memory location L(i+1) is less than the pulse baseline difference threshold value and i+1<n, then incrementing counter i by 1 and repeating (ii) starting at step (c), or if the absolute value of the difference between the voltage value stored in memory location L(i) and the voltage value stored in memory location L(i+1) is less than the pulse baseline difference threshold value and i+1=n, then calculating an average value of the voltage values stored in memory locations L(1) to L(n), storing the average value in memory as the current pulse baseline value, shifting the voltage values stored in memory locations L(2) to L(n) to memory locations L(1) to L(n−1), and repeating (ii) starting at step (c), or if the absolute value of the difference between the voltage value stored in memory location L(i) and the voltage value stored in memory location L(i+1) is not less than the pulse baseline difference threshold value, repeating (ii) starting at step (a).

2. The pulse baseline value calculation method according to claim 1, wherein n is $2^m$, and the value of m is selected from 2, 3, 4 or 5.

3. The pulse baseline value calculation method according to claim 1, wherein the pulse baseline difference threshold value is from 10-30.

4. The pulse baseline value calculation method according to claim 1, wherein a pulse starting point is identified according to one of the following methods:

(1) if w consecutive voltage values successively and progressively increase, and the difference value between the wth voltage value and the first voltage value in the w voltage values is greater than a predetermined starting point threshold value, then the pulse starting point is the first voltage value of the w consecutive voltage values; or (2) if the jth datum of the w consecutive voltage values progressively decreases, the other consecutive voltage values progressively increase, meanwhile the (j+1)th voltage value is greater than the (j−1)th voltage value, and the difference value between the wth voltage value and the first voltage value in the w consecutive voltage values is greater than the predetermined starting point threshold, then the pulse starting point is the first datum of the w consecutive voltage values.

5. The pulse baseline value calculation method according to claim 4, wherein w is an integer of 5-10.

6. The pulse baseline value calculation method according to claim 5, wherein the pulse baseline difference threshold value is from 20-60.

\* \* \* \* \*